United States Patent [19]
Hanatani et al.

[11] Patent Number: 5,213,926
[45] Date of Patent: May 25, 1993

[54] PHENYLENEDIAMINE DERIVATIVE AND PHOTOSENSITIVE MATERIAL USING SAID DERIVATIVE

[75] Inventors: Yasuyuki Hanatani, Sakai; Hiroaki Iwasaki, Hirakata, both of Japan

[73] Assignee: Mita Industrial Co., Ltd., Osaka, Japan

[21] Appl. No.: 856,686

[22] Filed: Mar. 24, 1992

[30] Foreign Application Priority Data

Mar. 29, 1991 [JP] Japan .................................. 3-66765

[51] Int. Cl.$^5$ ...................... G03G 5/047; G03G 5/09; C07C 211/00
[52] U.S. Cl. ........................................ 430/59; 430/83; 564/305
[58] Field of Search ...................... 430/59, 83; 564/305

[56] References Cited
U.S. PATENT DOCUMENTS

| | | | |
|---|---|---|---|
| 3,211,793 | 10/1965 | Roos ................................ | 564/305 X |
| 4,150,987 | 4/1979 | Anderson et al. ................. | 430/59 |
| 5,004,662 | 4/1991 | Mutoh et al. ..................... | 430/59 |
| 5,059,503 | 10/1991 | Muto et al. ...................... | 430/83 |
| 5,087,544 | 2/1992 | Muto et al. ...................... | 430/83 |

FOREIGN PATENT DOCUMENTS

| | | |
|---|---|---|
| 54-59143 | 5/1979 | Japan . |
| 99447 | 6/1983 | Japan ..................... 430/59 |
| 1-142642 | 6/1989 | Japan . |
| 2-210451 | 8/1990 | Japan . |

Primary Examiner—Roland Martin
Attorney, Agent, or Firm—Beveridge, DeGrandi, Weilacher & Young

[57] ABSTRACT

The present invention provides a phenylenediamine derivative of the following general formula (1). This derivative is excellent in photostability. Accordingly, when this derivative is contained in a photosensitive layer as an electric charge transferring material, there may be obtained an electrophotosensitive material excellent in photostability.

General Formula (1):

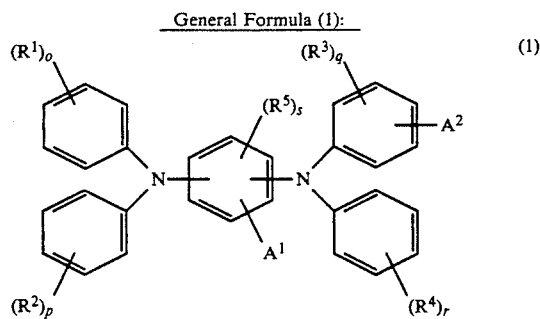

[wherein $R^1$, $R^2$, $R^3$, $R^4$ and $R^5$ are the same as or different from one another.

Each of $A^1$ and $A^2$ is a hydrogen atom or the following group:

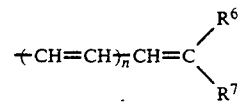

(wherein $R^6$ and $R^7$ are the same as or different from each other, and each is a hydrogen atom, an alkyl group, an alkoxy group, an aryl group, an aralkyl group or a heterocyclic group; the alkyl group, the alkoxy group, the aryl group, the aralkyl group and the heterocyclic group may have respective substituting groups; n is 0 or 1. $A^1$ and $A^2$ are not hydrogen atoms simultaneously. $R^6$ and $R^7$ are not hydrogen atoms simultaneously.)]

10 Claims, No Drawings

PHENYLENEDIAMINE DERIVATIVE AND PHOTOSENSITIVE MATERIAL USING SAID DERIVATIVE

BACKGROUND OF THE INVENTION

The present invention relates to a phenylenediamine derivative suitable for an electric charge transferring material in a photosensitive material, and also relates to a photosensitive material using such a derivative.

As a photosensitive material in an image forming apparatus such as an electrophotographic copying apparatus, there has recently and widely been used an organic photosensitive material which is excellent in machinability and advantageous in production cost and which offers a great degree of freedom for design of performance.

For forming a copied image with the use of a photosensitive material, the Carlson process is widely used. The Carlson process comprises the steps of uniformly charging a photosensitive material with electricity by corona discharge, exposing the charged photosensitive material to a document image, thereby to form an electrostatic latent image corresponding to the document image, developing the electrostatic latent image by a toner containing developer, thereby to form a toner image, transferring the toner image to paper or the like, fixing the toner image thus transferred, and cleaning the photosensitive material to remove toner remaining thereon after the toner image has been transferred. To form an image of high quality in the Carlson process, it is required that the photosensitive material is excellent in charging and photosensitive characteristics and presents a low residual potential after exposed to light.

Conventionally, there have been known inorganic photoconductive materials such as selenium, cadmium sulfide and the like as photosensitive materials. However, these inorganic photoconductive materials are toxic and need great production costs.

There has been proposed a so-called organic photosensitive material using various organic substances in place of the above-mentioned inorganic substances. Such an organic photosensitive material has a photosensitive layer comprised of an electric charge generating material for generating electric charges by light exposure and an electric charge transferring material having a function of transferring the electric charges thus generated.

To meet various requirements for the organic photosensitive material, it is necessary to properly photosensitive material, it is necessary to properly select the electric charge generating material and the electric charge transferring material. As the electric charge transferring material, there have been proposed and put on the market a variety of organic compounds such as polyvinyl carbazole, oxadiazole compounds, pyrazoline compounds, hydrazone compounds and the like. By way of example, there have been known hydrazone compounds disclosed in Japanese Unexamined Patent Publications Nos. 59143/1979 and 210451/1990.

In the electric charge transferring materials above-mentioned, however, the drift mobility representing the electric charge transferring ability is relatively small. Further, since the dependency of the drift mobility upon the electric field intensity is great, the movement of an electric charge in a low electric field is small. This makes it difficult that the residual potential disappears. Further, such materials are disadvantageously apt to be deteriorated due to irradiation of ultraviolet rays.

In view of the problems above-mentioned, there has been proposed N,N,N',N'-tetraphenyl-1,3-phenylenediamine as an example of a m-phenylenediamine derivative of which dependency of the drift mobility upon the electric field intensity is small and which has a good compatibility with respect to a resin (Japanese Unexamined Patent Publication No. 142642/1989). Such a m-phenylenediamine derivative presents good light-exposure properties with respect to ultraviolet rays and the like. When actually used in an electrophotographic copying apparatus, this derivative presents stable characteristics. However, if this derivative is exposed to light for a long period of time or at a high temperature in case of trouble of the copying apparatus, this derivative is disadvantageously damaged in an irrecoverable extent. Further, this derivative does not have sufficient sensitivity and repeat characteristics.

SUMMARY OF THE INVENTION

It is an object of the present invention to provide a phenylenediamine derivative suitable for an electric charge transferring material.

It is another object of the present invention to provide a photosensitive material excellent in sensitivity and repeat characteristics.

The decrease in characteristics of a photosensitive material due to light exposure is generally caused by the formation, in the photosensitive material, of impurities which constitute a trap for the electric charge transferring material. In the m-phenylenediamine derivative, a ring-closure reaction made between the center benzene ring and other phenyl groups is considered to be such a photo-deterioration reaction. It is believed that this ring-closure reaction is apt to take place because the electron density of molecules in the phenylenediamine derivative is biased to the center benzene ring. Accordingly, the inventors of the present invention have considered that, when a phenyl group added to a nitrogen atom of the center benzene ring is substituted for a predetermined substituting group, or the center benzene ring is substituted for a substituting group, the reactivity of the phenylenediamine derivative may be restrained, thereby to improve photostability. After having conducted a variety of tests, the inventors have found the novel fact that, when the phenyl group or the center benzene ring is substituted for a predetermined substituting group, the photosensitive material can effectively be improved in photostability without injury to the electric charge transferring characteristics such as drift mobility and the like.

Accordingly, the phenylenediamine derivative of the present invention is represented by the following general formula (1):

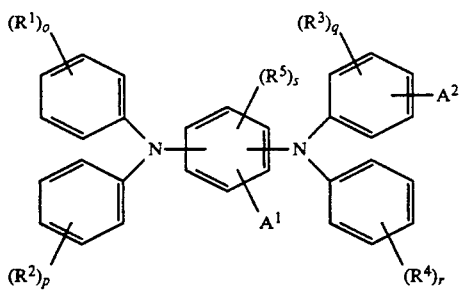

(1)

[wherein $R^1$, $R^2$, $R^3$, $R^4$ and $R^5$ are the same as or different from one another, and each is a hydrogen atom, a halogen atom, an alkyl group, an alkoxy group, an aryl group, an aralkyl group or a heterocyclic group; the alkyl group, the alkoxy group, the aryl group, the aralkyl group and the heterocyclic group may have respective substituting groups; o, p, q, r and s are the same as or different from one another, and each is an integer from 0 to 2.

Each of $A^1$ and $A^2$ is a hydrogen atom or the following group:

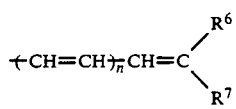

(wherein $R^6$ and $R^7$ are the same as or different from each other, and each is a hydrogen atom, an alkyl group, an alkoxy group, an aryl group, an aralkyl group or a heterocyclic group; the alkyl group, the alkoxy group, the aryl group, the aralkyl group and the heterocyclic group may have respective substituting groups; n is 0 or 1. $A^1$ and $A^2$ are not hydrogen atoms simultaneously. $R^6$ and $R^7$ are not hydrogen atoms simultaneously.)]

In the phenylenediamine derivative (1) of the present invention, a phenyl group is added to each nitrogen atom of the center benzene ring. Accordingly, a reaction point is protected, causing the derivative to be hardly attacked by an oxide or the like. This restrains the ring-closure reaction between the center benzene ring and other groups to improve the photostability.

The photosensitive material containing the phenylenediamine derivative represented by the general formula (1) is less damaged by light-exposure for a long period of time or at a high temperature, than a conventional photosensitive material, and is therefore excellent in photostability.

Further, the phenylenediamine derivative represented by the general formula (1) is excellent in electric charge transferring ability. Accordingly, the phenylenediamine derivative is contained in a photosensitive layer as an electric charge transferring material, so that there may be obtained a photosensitive material excellent in sensitivity, charging ability and repeat characteristics.

DETAILED DESCRIPTION OF THE INVENTION

Examples of the halogen atom include fluorine, chlorine, bromine and iodine.

Examples of the alkyl group include a lower alkyl group having 1 to 6 carbon atoms, such as methyl, ethyl, propyl, isopropyl, butyl, isobutyl, t-butyl, pentyl and hexyl groups.

Examples of the alkoxy group include a lower alkoxy group having 1 to 6 carbon atoms in its alkyl portion, such as methoxy, ethoxy, isopropoxy, butoxy, t-butoxy, pentyloxy and hexyloxy groups.

Examples of the aryl group include phenyl, biphenyl, naphthyl, anthryl and phenanthryl groups.

Examples of the aralkyl group include benzyl, α-phenethyl, β-phenethyl, 3-phenylpropyl, benzhydryl, and trityl groups.

Examples of the heterocyclic group include thienyl, pyrrolyl, pyrrolidinyl, oxazolyl, isooxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino, and thiazolyl groups. Further, the heterocyclic group may be condensed with an aromatic ring.

Examples of the substituting group include a halogen atom, an amino group, a hydroxyl group, a carboxyl group which may be esterificated, a cyano group, an alkyl group having straight-chain or branched 1 to 6 carbon atoms, an alkoxy group having straight-chain or branched 1 to 6 carbon atoms, and an alkenyl group having straight-chain or branched 2 to 6 carbon atoms which sometimes has an allyl group.

Preferably, the phenylenediamine derivative (1) of the present invention has a nitrogen atom added to the center benzene ring in a metha position in order to obtain a photosensitive material excellent in sensitivity and repeat characteristics.

As specific examples of the phenylenediamine derivative of the general formula (1), the following compounds (2) to (23) are mentioned.

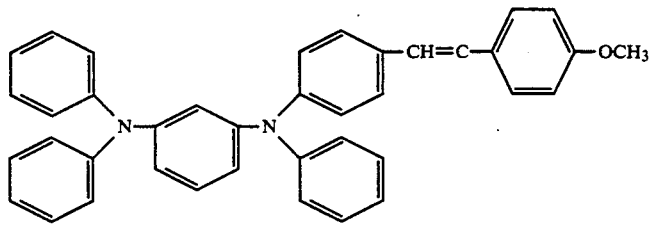

(2)

-continued
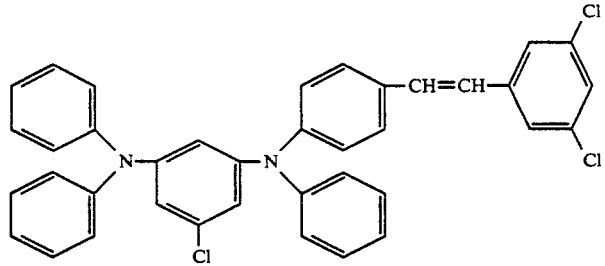 (3)
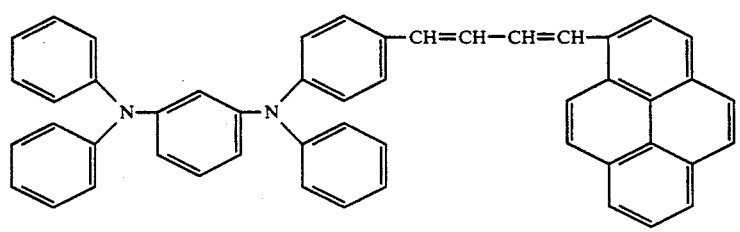 (4)
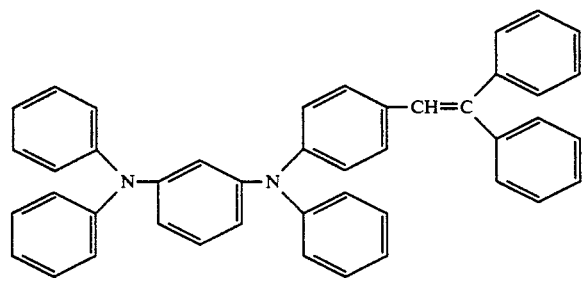 (5)
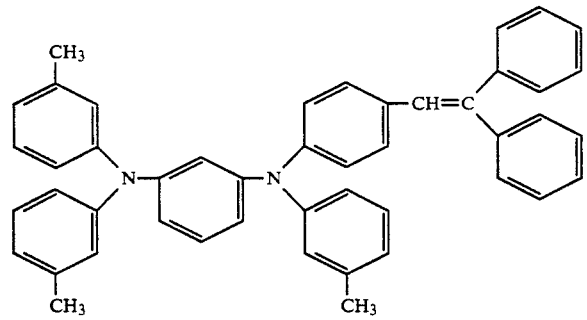 (6)
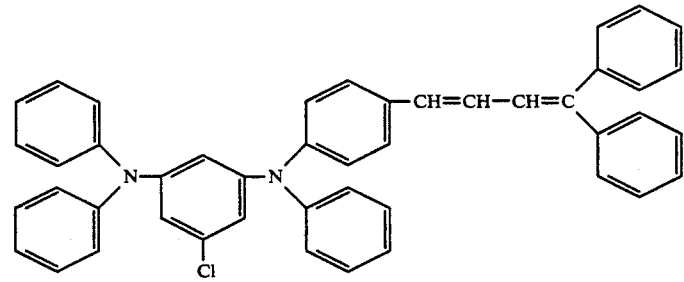 (7)
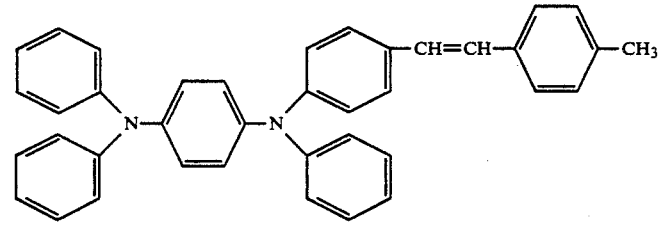 (8)

-continued
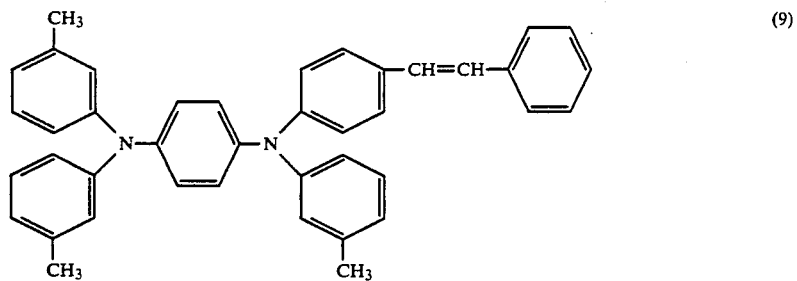
(9)
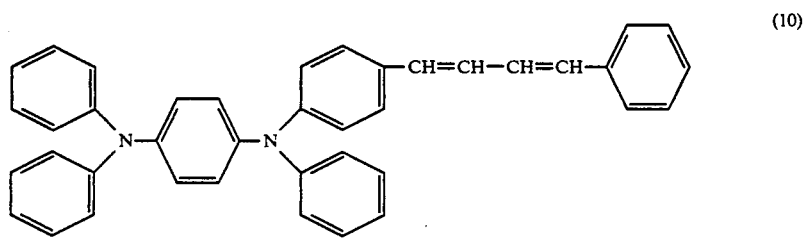
(10)
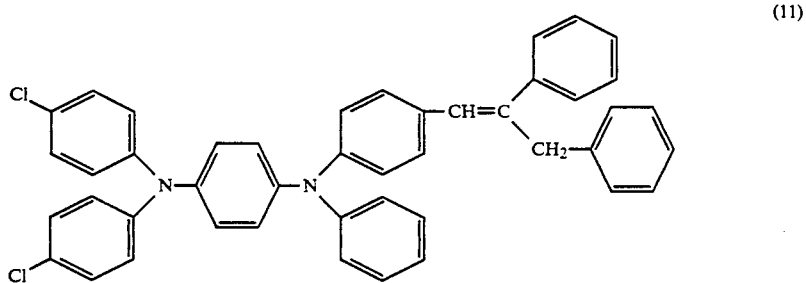
(11)
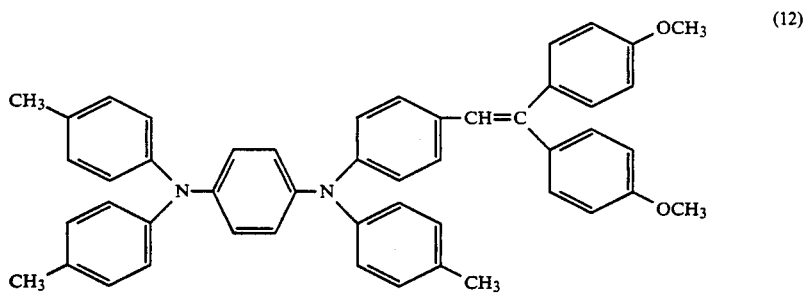
(12)
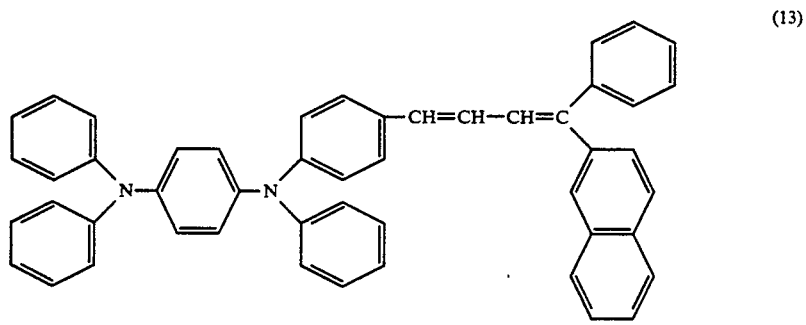
(13)

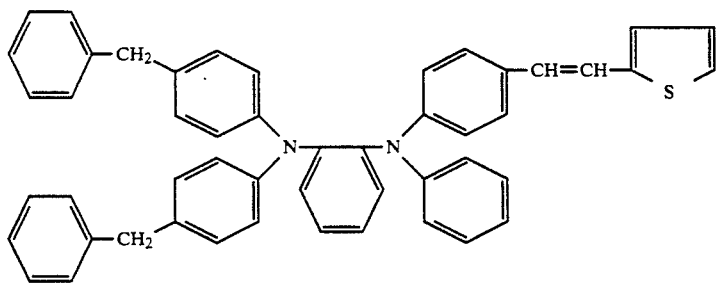
(14)
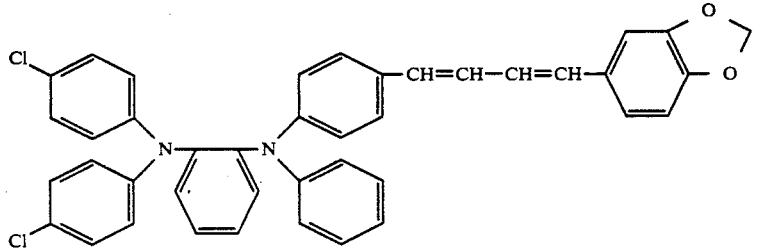
(15)
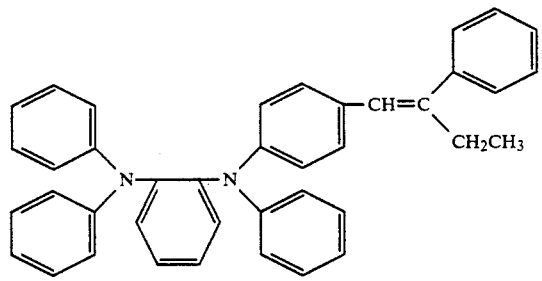
(16)
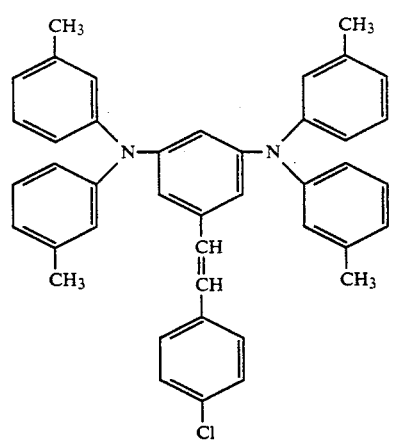
(17)
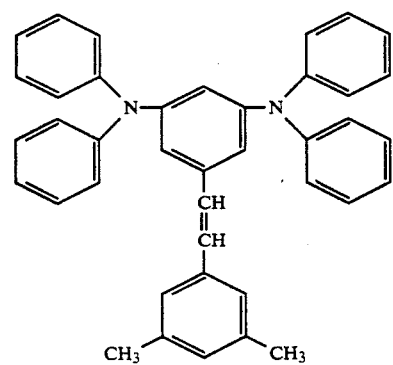
(18)

-continued
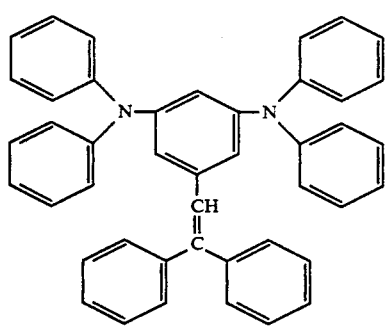
(19)
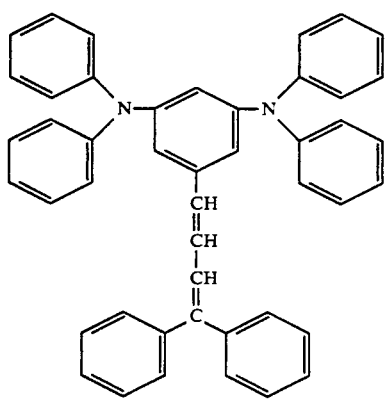
(20)
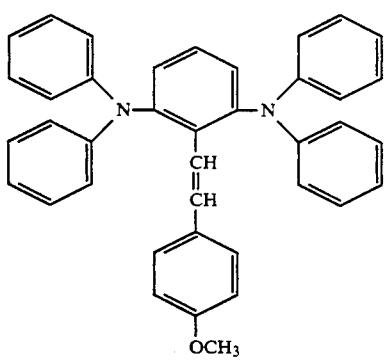
(21)
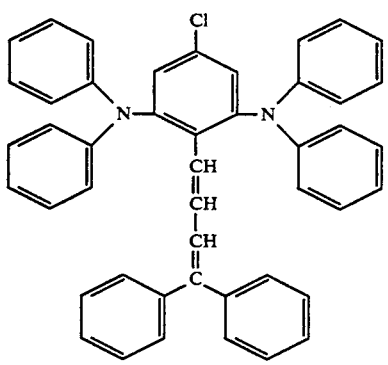
(22)

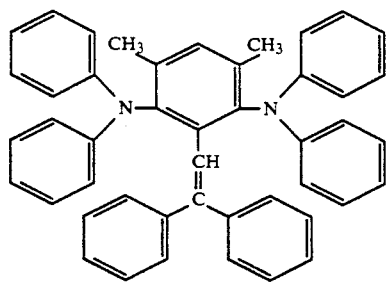

(23)

The phenylenediamine derivative of the present invention may be composed in any of a variety of manners, and may be composed, for example, by the following reaction formula.

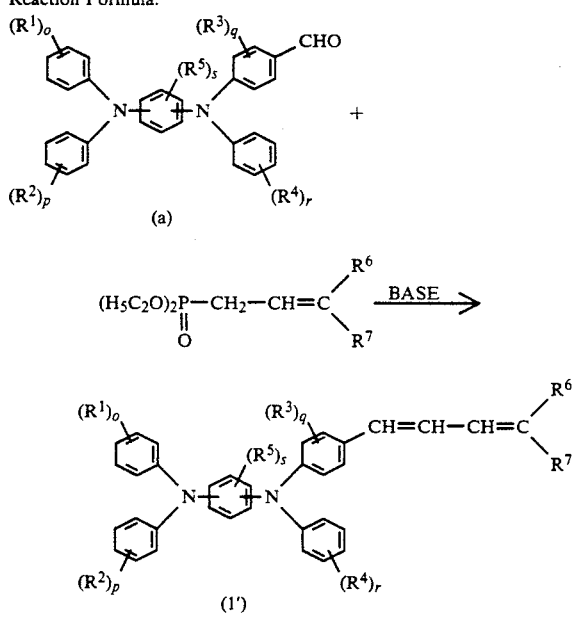

(wherein $R^1$, $R^2$, $R^3$, $R^4$, $R^5$, $R^6$ and $R^7$ are the same as mentioned above.)

In the reaction formula above-mentioned, an aldehyde compound of the formula (a) and a dialkyl phosphorous acid compound of the formula (b) are reacted in an organic solvent such as DMF, nitrobenzene, THF or dioxane in the presence of basishes compounds (for example, $C_6H_5Li$, NaOH or the like), thereby to give the phenylenediamine derivative of the formula (1') in accordance with the present invention.

The aldehyde compound (a) and the dialkyl phosphorous acid compound (b) are reacted at about 10° to 150° C. at equal molar quantities, thereby to give the phenylenediamine derivative of the formula (1') in accordance with the present invention.

The phenylenediamine compound of the general formula (1) serving as the electric charge transferring material may be contained, in a binding resin, alone or in combination with the other conventional electric charge transferring material, thereby to form a photosensitive layer. As the conventional electric charge transferring material, there may be used various electron attractive or donative compounds.

Examples of the electron attractive compound include a diphenoquinone derivative such as 2,6-dimethyl-2',6'-di(tert-dibutyl)diphenoquinone or the like, malononitrile, a thiopyran compound, tetracyanoethylene, 2,4,8-trinitrothioxanthene, 3,4,5,7-tetranitro-9-fluorenone, dinitrobenzene, dinitroanthracene, dinitroacridine, nitroanthraquinone, dinitroanthraquinone, succinic anhydride, maleic anhydride, dibromo maleic anhydride and the like.

Examples of the electron donative compound include nitrogen-containing cyclic compounds and condensed polycylic compounds which include oxadiazole compounds such as 2,5-di(4-methylaminophenyl), 1,3,4-oxadiazole and the like, styryl compounds such as 9-(4-diethylaminostyryl)anthracene and the like, carbazole compounds such as polyvinyl carbazole and the like, pyrazoline compounds such as 1-phenyl-3-(p-dimethylaminophenyl)pyrazoline and the like, hydrazone compounds, triphenylamine compounds, indole compounds, oxazole compounds, isooxazole compounds, thiazole compounds, thiadiazole compounds, imidazole compounds, pyrazole compounds, triazole compounds and the like.

These examples of the electric charge transferring material may be used alone or in combination of plural types. When there is used the electric charge transferring material having film-forming properties such as polyvinyl carbazole or the like, a binding resin is not necessarily required.

The photosensitive layer of the present invention can be applied to both a single-layer type including an electric charge generating material, a compound of the general formula (1) serving as an electric charge transferring material and a binding resin, and a multi-layer type in which an electric charge generating layer and an electric charge transferring layer are laminated.

To form a single-layer type photosensitive material, there may be formed, on a conductive substrate, a photosensitive layer containing the compound of the general formula (1) serving as an electric charge transferring material, an electric charge generating material, a binding resin and the like.

To form a multi-layer type photosensitive material, an electric charge generating layer containing an electric charge generating material is formed on the conductive substrate by vapor deposition, coating or the like, and an electric charge transferring layer containing the compound of the general formula (1) serving as the electric charge transferring material and a binding resin is then formed on the electric charge generating layer. On the contrary, the electric charge transferring layer similar to that above-mentioned may be formed on the conductive substrate, and the electric charge generating layer containing an electric charge generating material may then be formed on the electric charge transferring layer by vapor deposition, coating or the like. Alternately, the electric charge generating layer may be formed by coating a binding resin containing an electric charge generating material and an electric charge transferring material as dispersed therein.

Examples of the electric charge generating material include selenium, selenium-tellurium, selenium-arsenic, amorphous silicon, pyrylium salt, azo compounds, disazo compounds, phthalocyanine compounds, anthanthrone compounds, indigo compounds, triphenylmethane compounds, threne compounds, toluidine compounds, pyrazoline compounds, perylene compounds, quinacridon compounds, pyrrolopyrrole compounds and the like, which have conventionally been used. These examples may be used alone or in combination of plural types to present an absorption wavelength in a desired range.

As the binding resin of the single- or multi-layer type photosensitive layer, any of a variety of resins may be used. Examples of the binding resin include various polymers which include: thermoplastic resins such as a styrene polymer, a styrene-butadiene copolymer, a styrene-acrylonitrile copolymer, a styrene-maleic acid copolymer, an acrylic copolymer, a styrene-acrylic acid copolymer, polyethylene, an ethylene vinyl acetate copolymer, chlorinated polyethylene, polyvinyl chloride, polypropylene, a vinyl chloridevinyl acetate copolymer, polyester, alkyd resin, polyamide, polyurethane, polycarbonate, polyallylate, polysulfon, diallyl phthalate resin, ketone resin, polyvinyl butyral resin, polyether resin and the like; crosslinking thermosetting resins such as silicone resin, epoxy resin, phenol resin, urea resin, melamine resin and the like; photosetting resins such as epoxy-acrylate, urethane-acrylate and the like. These polymers may be used alone or in combination of plural types.

When the electric charge generating layer and the electric charge transferring layer are formed with coating means, a solvent is used for preparing a coating solution. As such a solvent, there may be used any of a variety of organic solvents. Examples of such organic solvents include: alcohols such as methanol, ethanol, isopropanol, butanol and the like; aliphatic hydrocarbons such as n-hexane, octane, cyclohexane and the like; aromatic hydrocarbons such as benzene, toluene, xylene and the like; halogenated hydrocarbons such as dichloromethane, dichloroethane, carbon tetrachloride, chlorobenzene and the like; ethers such as a dimethyl ether, diethyl ether, tetrahydrofuran, ethylene glycol dimethyl ether, diethylene glycol dimethyl ether and the like; ketones such as acetone, methylethyl ketone, cyclohexanone and the like; esters such as ethyl acetate, methyl acetate and the like; dimethylformaldehyde; dimethylformamide; dimethylsulfoxide and the like. These solvents may be used alone or in combination of plural types.

To improve the electric charge generating layer in sensitivity, there may be used a conventional sensitizer such as tert-phenyl, halonaphtoquinone, acenaphthylene or the like, together with the electric charge generating material.

To improve the electric charge transferring and generating materials in dispersibility, aplicability and the like, there may be used a surfactant, a levelling agent and the like.

As the conductive substrate, any of a variety of conductive materials may be used, which include: single metal such as aluminium, copper, tin, platinum, silver, vanadium, molybdenum, chromium, cadmium, titanium, nickel, paradium, indium, stainless copper, brass and the like; plastic material vapor-deposited or laminated with any of the metals above-mentioned; glass material coated with aluminium iodide, tin oxide, indium oxide or the like.

The conductive substrate may be made in the form of a sheet or a drum. The substrate itself may be conductive or only the surface of the substrate may be conductive. Preferably, the conductive substrate has a sufficient mechanical strength when used.

In the multi-layer type photosensitive material, the electric charge generating material forming the electric charge generating layer and the binding resin may be used at a variety of ratios. Preferably 5 to 500 parts by weight and more preferably 10 to 250 parts by weight of the electric charge generating material may be used for 100 parts by weight of the binding resin. The thickness of the electric charge generating layer is optional, but is preferably from 0.01 to 5 $\mu$m and more preferably from 0.1 to 3 $\mu$m.

The phenylenediamine derivative (electric charge transferring material) of the general formula (1) forming an electric charge transferring layer and the binding resin may be used at a variety of ratios within such a range as not to prevent the transmission of the electric charge and as to prevent the crystallization of the electric charge transferring material. Preferably 25 to 200 parts by weight and more preferably 50 to 150 parts by weight of the phenylenediamine derivative of the general formula (1) may be used for 100 parts by weight of the binding resin such that electric charges generated on the electric charge generating layer can easily be transferred by light radiation. The thickness of the electric charge transferring layer is preferably from 2 to 100 $\mu$m and more preferably from 5 to 30 $\mu$m.

In the single-layer type photosensitive material, preferably 2 to 20 parts by weight and more preferably 3 to 15 parts by weight of the electric charge generating material, and preferably 40 to 200 parts by weight and more preferably 50 to 150 parts by weight of the phenylenediamine derivative (electric charge transferring material) of the general formula (1) may be used for 100 parts by weight of the binding resin. The thickness of the single-layer type photosensitive layer is preferably from 10 to 50 $\mu$m and more preferably from 15 to 30 $\mu$m.

A barrier layer may be formed, in such a range as not to injure the characteristics of the photosensitive material, between the conductive substrate and the photosensitive layer in the single-layer type photosensitive material, or between the conductive substrate and the electric charge generating layer, between the conductive substrate and the electric charge transferring layer and between the electric charge generating layer and the electric charge transferring layer in the multi-layer type photosensitive material. Further, a protective layer may be formed on the surface of the photosensitive material.

When the electric charge generating layer and the electric charge transferring layer are formed by a coating method, the electric charge generating material, the binding resin and the like may be prepared as dispersed and mixed with the use of any of conventional methods, for example, a roll mill, a ball mill, an atriter, a paint shaker, a supersonic dispenser or the like, thereby to prepare a coating solution. Then, the coating solution may be applied with the use of any of conventional coating methods, and then allowed to dry. As mentioned earlier, the electric charge generating layer may be formed by vapor-depositing the electric charge generating material.

EXAMPLES

The following description will discuss in detail the present invention with reference to examples and comparative examples thereof.

(1) Synthesis Examples of Electric Charge Transferring Material

EXAMPLE 1

Synthesis of a phenylenediamine derivative represented by the formula (2)

In the presence of 20 g of basishes compounds (t-butoxypotassium), 44.1 g of an aldehyde compound of the following formula (24) and 24.2 g of a dialkyl phosphorous acid compound of the following formula (25) were reacted in 2,000 ml of DMF at 50° C. for 12 hours. The resultant product was isolated by recrystallizing operation to give a phenylenediamine derivative of the formula (2).

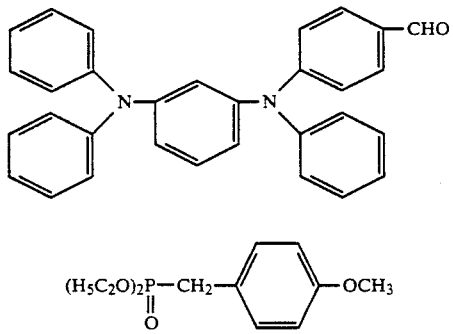

(24)

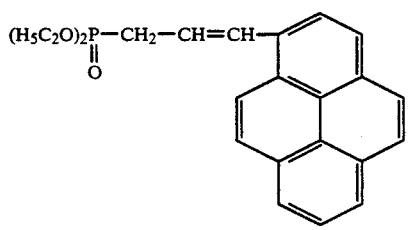

(25)

The resultant phenylenediamine derivative had a yield of 26%. The following shows the results of elemental analysis.

In $C_{39}H_{31}N_2$: Calculation Values-C:86.16%, H:5.75%, N:5.15%; Measured Values-C:86.32%, H:5.66%, N:5.08%.

EXAMPLE 2

Synthesis of a phenylenediamine derivative represented by the formula (4)

A phenylenediamine derivative of the formula (4) was prepared in the same manner as in Example 1 except that 37.8 g of a dialkyl phosphorous acid compound of the following formula (27) was used in place of a dialkyl phosphorous acid compound of the formula (25).

(27)

The resultant phenylenediamine derivative had a yield of 20%. The following shows the results of elemental analysis.

In $C_{49}H_{41}N_2$: Calculation Values-C:90.33%, H:5.46%, N:4.21%; Measured Values-C:90.28%, H:5.54%, N:4.18%.

EXAMPLE 3

Synthesis of a phenylenediamine derivative represented by the formula (5)

A phenylenediamine derivative of the formula (5) was prepared in the same manner as in Example 1 except that 28.0 g of a dialkyl phosphorous acid compound of the following formula (29) was used in place of a dialkyl phosphorous acid compound of the formula (25).

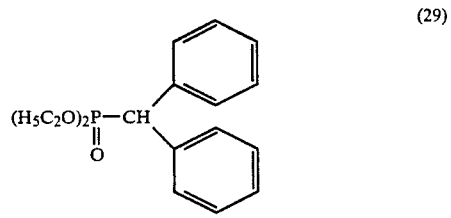

(29)

The resultant phenylenediamine derivative had a yield of 30%. The following shows the results of elemental analysis.

In $C_{44}H_{29}N_2$: Calculation Values-C:89.46%, H:5.80%, N:4.74%; Measured Values-C:89.32%, H:5.87%, N:4.81%.

EXAMPLE 4

Synthesis of a phenylenediamine derivative represented by the formula (6)

A phenylenediamine derivative of the formula (6) was prepared in the same manner as in Example 1 except that 46.7 g of an aldehyde compound of the following formula (30) was used in place of an aldehyde compound of the formula (24), and 28.0 g of a dialkyl phosphorous acid compound of the following formula (31) was used in place of a dialkyl phosphorous acid compound of the formula (25).

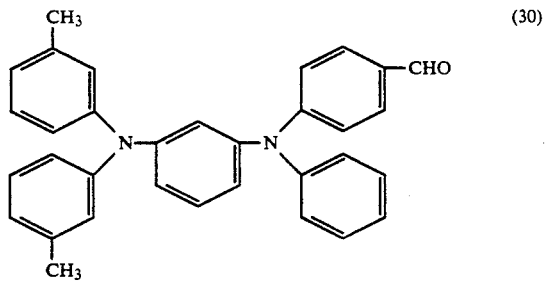

(30)

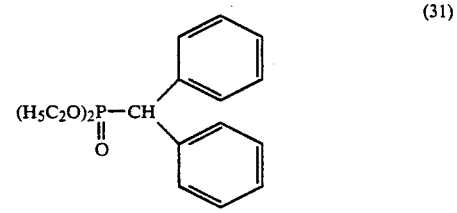

(31)

The resultant phenylenediamine derivative had a yield of 36%. The following shows the results of elemental analysis.

In $C_{52}H_{50}N_2$: Calculation Values-C:89.20%, H:6.37%, N:4.43%; Measured Values-C:89.33%, H:6.30%, N:4.37%.

EXAMPLE 5

Synthesis of a phenylenediamine derivative represented by the formula (12)

A phenylenediamine derivative of the formula (12) was prepared in the same manner as in Example 1 except that 46.7 g of an aldehyde compound of the following formula (32) was used in place of an aldehyde compound of the formula (24), and 30.6 g of a dialkyl phosphorous acid compound of the following formula (33) was used in place of a dialkyl phosphorous acid compound of the formula (25).

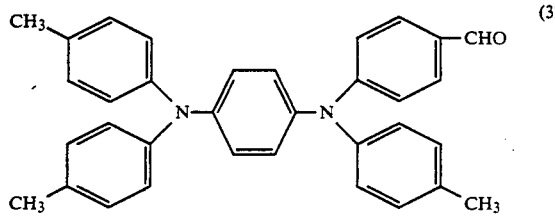

(32)

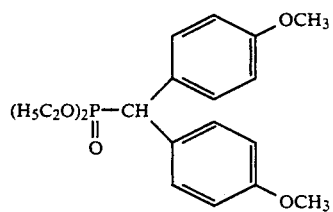

(33)

The resultant phenylenediamine derivative had a yield of 22%. The following shows the results of elemental analysis.

In $C_{54}H_{54}N_2$: Calculation Values-C:89.05%, H:6.71%, N:4.24%; Measured Values-C:88.97%, H:6.70%, N:4.33%.

EXAMPLE 6

Synthesis of a phenylenediamine derivative represented by the formula (18)

A phenylenediamine derivative of the formula (18) was prepared in the same manner as in Example 1 except that 44.1 g of an aldehyde compound of the following formula (34) was used in place of an aldehyde compound of the formula (24), and 30.8 g of a dialkyl phosphorous acid compound of the following formula (35) was used in place of a dialkyl phosphorous acid compound of the formula (25).

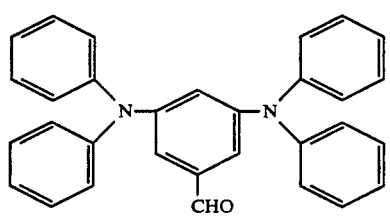

(34)

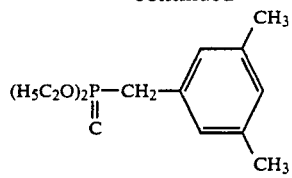

(35)

The resultant phenylenediamine derivative had a yield of 36%. The following shows the results of elemental analysis.

In $C_{40}H_{34}N_2$: Calculation Values-C:88.53%, H:6.31%, N:5.16%; Measured Values-C:88.64%, H:6.24%, N:5.12%.

EXAMPLE 7

Synthesis of a phenylenediamine derivative represented by the formula (19)

A phenylenediamine derivative of the formula (19) was prepared in the same manner as in Example 1 except that 44.1 g of an aldehyde compound of the following formula (36) was used in place of an aldehyde compound of the formula (24), and 28.0 g of a dialkyl phosphorous acid compound of the following formula (37) was used in place of a dialkyl phosphorous acid compound of the formula (25).

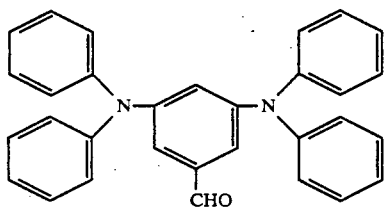

(36)

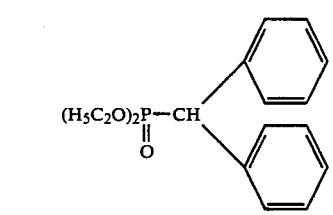

(37)

The resultant phenylenediamine derivative had a yield of 32%. The following shows the results of elemental analysis.

In $C_{44}H_{34}N_2$: Calculation Values-C:89.46%, H:5.80%, N:4.74%; Measured Values-C:89.60%, H:5.70%, N:4.70%.

EXAMPLE 8

Synthesis of a phenylenediamine derivative represented by the formula (20)

A phenylenediamine derivative of the formula (20) was prepared in the same manner as in Example 1 except that 44.1 g of an aldehyde compound of the following formula (38) was used in place of an aldehyde compound of the formula (24), and 29.4 g of a dialkyl phosphorous acid compound of the following formula (39) was used in place of a dialkyl phosphorous acid compound of the formula (38)

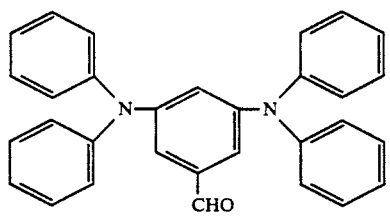

(39)

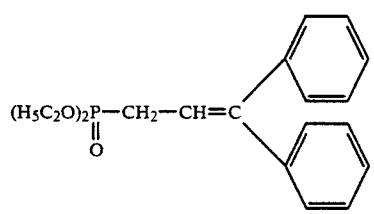

The resultant phenylenediamine derivative had a yield of 26%. The following shows the results of elemental analysis.

In $C_{46}H_{36}N_2$: Calculation Values-C:89.57%, H:5.88%, N:4.55%; Measured Values-C:89.41%, H:5.76%, N:4.59%.

(2) Preparation of Electrophotosensitive Material

Preparation of Multi-Layer Type Electrophotosensitive Material

EXAMPLES 9 to 13 AND COMPARATIVE EXAMPLES 1 AND 2

2 Parts by weight of the electric charge generating material, 1 part by weight of a polyvinyl butyral resin ("S-lecBM-5" manufactured by Sekisui Kagaku Kogyo Co., Ltd.) and 120 parts by weight of tetrahydrofuran were dispersed for 2 hours by means of a paint shaker using zirconia beads (having a diameter of 2 mm). The dispersing solution thus prepared was applied, by means of a wire bar, to an aluminium sheet, which was then dried at 100° C. for 1 hour. Thus, an electric charge generating layer with a thickness of 0.5 μm was formed. The electric charge generating materials which were used are shown in Tables 1 and 2. In Tables 1 and 2, the electric charge generating materials A, B and C of the examples are compounds represented by the following formulas (A), (B) and (C).

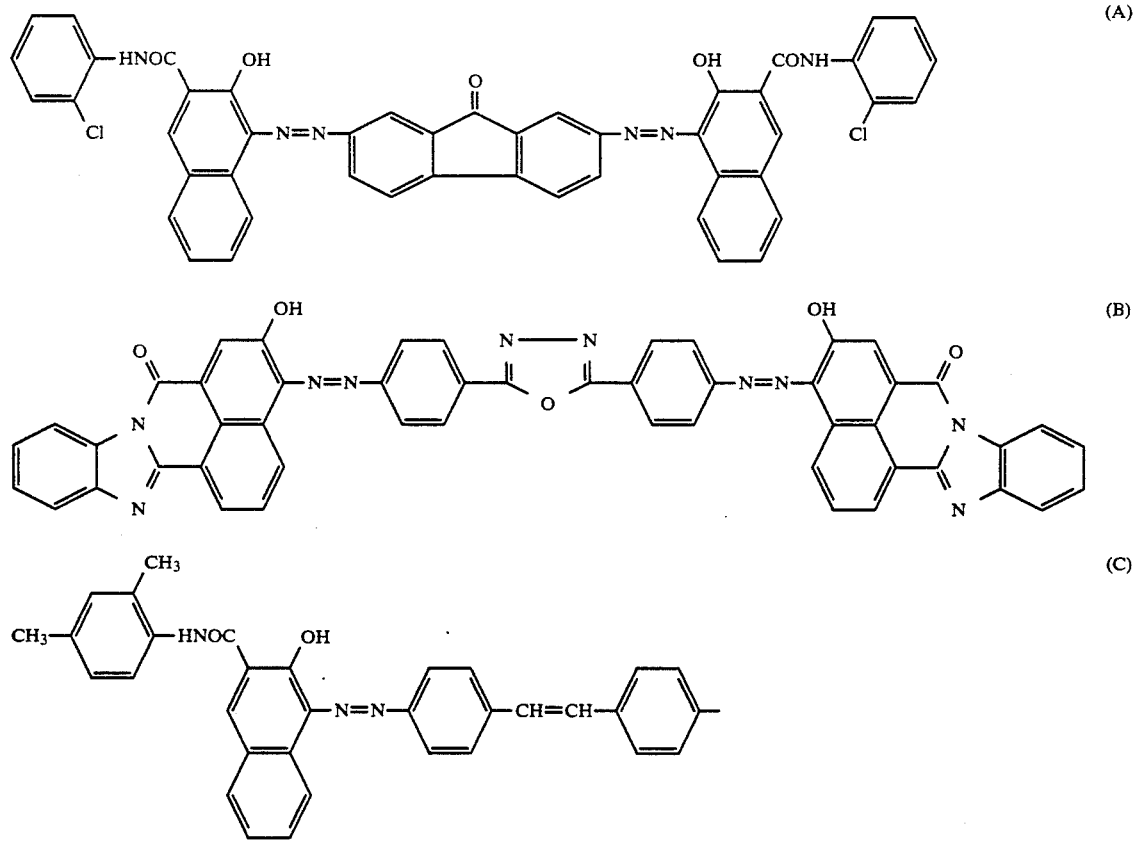

-continued

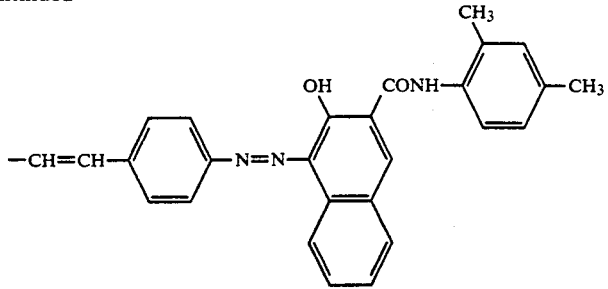

1 Part by weight of the electric charge transferring material and 1 part by weight of a polycarbonate resin ("Z-300" manufactured by Mitsubishi Gas Kagaku Kogyo Co., Ltd.) were dissolved in 9 parts by weight of toluene. The solution thus prepared was applied, by means of the wire bar, to the electric charge generating layer, which was then dried at 100° C. for 1 hour. Thus, an electric charge transferring layer with a thickness of 22 μm was formed. In Tables 1 and 2, the electric charge transferring materials used in Examples 9 to 13 are represented by compound numbers shown in the above-mentioned specific examples. The electric charge transferring materials I and II used in Comparative Examples 1 and 2 are compounds represented by the following formulas (I) and (II).

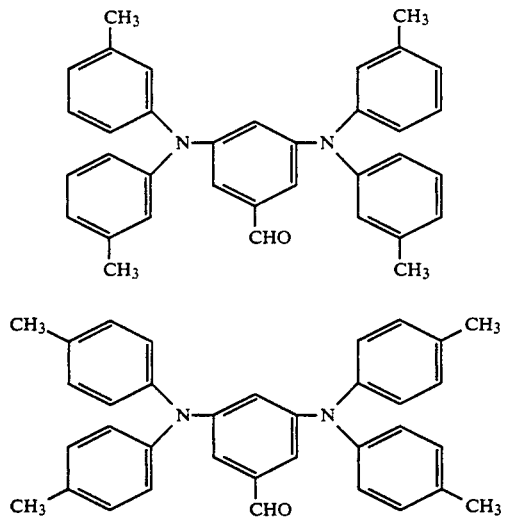

Preparation of Single-Layer Type Electrophotosensitive Material

EXAMPLES 14 TO 16 AND COMPARATIVE EXAMPLES 3 AND 4

1 Part by weight of the electric charge generating material and 60 parts by weight of tetrahydrofuran were dispersed for 2 hours by means of a paint shaker using zirconia beads (having a diameter of 2 mm). To the dispersing solution thus prepared are added 50 parts by weight of a tetrahydrofuran solution of a polycarbonate resin having 20% by weight of a solid content ("Z-300" manufactured by Mitsubishi Gas Kagaku Kogyo Co., Ltd.) and 10 parts by weight of the electric charge transferring material, which were further dispersed for 1 hour. The dispersing solution thus prepared was applied, by means of a wire bar, to an aluminum sheet, which was then dried at 100° C. for 1 hour. Thus, a photosensitive layer with a thickness of 20 μm was formed. The electric charge generating and transferring materials which were used are indicated at respective chemical constitutional formula numbers in Tables 1 and 2 in the same manner as in the above-mentioned examples.

(3) Evaluation of the Electrophotosensitive Material

The surface potential, half-life light exposure ($E_{\frac{1}{2}}$) and residual potential of the photosensitive material obtained in the above-mentioned examples and comparative examples were measured by means of an evaluation tester ("EPA8100" manufactured by Kawaguchi Denki Co., Ltd.).

Measuring conditions are as follows.
Light Intensity: 50 lux
Exposure Intensity: 1/15 second
Surface Potential: A flowing current value was adjusted so as to approximate (±)700 V.
Light Source: Tungsten lamp
Electric Removal: 200 lux
Measurement of Residual Potential: Measurement was started after exposure continued for 0.2 second.

The test results of Examples 9 to 13 and Comparative Examples 1 and 2 for the multi-layer type photosensitive material and those of Examples 14 to 16 and Comparative Examples 3 and 4 for the single-layer type photosensitive material are shown in Tables 1 and 2, respectively.

TABLE 1

| | Electric charge transferring material | Electric charge generating material | Surface potential (V) | $E_{\frac{1}{2}}$ (lux · sec) | Residual potential (V) |
|---|---|---|---|---|---|
| Example 9 | 2 | A | −705 | 1.13 | −110 |
| Example 10 | 6 | A | −695 | 1.26 | −120 |
| Example 11 | 12 | A | −710 | 1.29 | −115 |
| Example 12 | 19 | B | −700 | 1.03 | −100 |
| Example 13 | 20 | C | −705 | 1.34 | −120 |
| Comparative Example 1 | I | A | −705 | 5.33 | −230 |
| Comparative Example 2 | II | A | −695 | 4.72 | −195 |

TABLE 2

| | Electric charge transferring material | Electric charge generating material | Surface potential (V) | $E_{\frac{1}{2}}$ (lux · sec) | Residual potential (V) |
|---|---|---|---|---|---|
| Example 14 | 4 | A | +710 | 1.44 | +125 |
| Example 15 | 5 | A | +715 | 1.52 | +130 |
| Example 16 | 18 | A | +710 | 1.37 | +125 |
| Comparative Example 3 | I | A | +700 | 4.67 | +255 |
| Comparative Example 4 | II | A | +700 | 5.26 | +265 |

As seen from these test results, the photosensitive material of each of Examples 9 to 16 has almost the same surface potential as the conventional photosensitive material (Comparative Examples 1 to 4), but is more excellent in half-life light exposure and residual potential and has its sensitivity remarkably improved.

What is claimed is:

1. A phenylenediamine derivative represented by the following general formula (1):

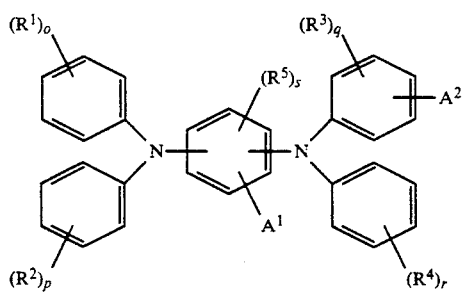

wherein $R^1$, $R^2$, $R^3$, $R^4$ and $R^5$ are the same as or different from one another, and each is a hydrogen atom, a halogen atom, an alkyl group, an alkoxy group, an aryl group, an aralkyl group or a heterocyclic group; the alkyl group, the alkoxy group, the aryl group, the aralkyl group and the heterocyclic group may have respective substituting groups; o, p, q, r and s are the same as or different from one another, and each is an integer from 0 to 2:

each of $A^1$ and $A^2$ is a hydrogen atom or the following group:

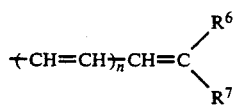

wherein $R^6$ and $R^7$ are the same as or different from each other, and each is a hydrogen atom, an alkyl group, an alkoxy group, an aryl group, an aralkyl group or a heterocyclic group; the alkyl group, the alkoxy group, the aryl group, the aralkyl group and the heterocyclic group may have respective substituting groups; n is 0 or 1; $A^1$ and $A^2$ are not hydrogen atoms simultaneously; $R^6$ and $R^7$ are not hydrogen atoms simultaneously.

2. A photosensitive material containing a conductive substrate having thereon a photosensitive layer which contains the phenylenediamine derivative (1) according to claim 1.

3. The photosensitive material according to claim 2, wherein the photosensitive layer is a multi-layer type photosensitive layer comprising an electric charge transferring layer on an electric charge generating layer which are laminated mutually.

4. The multi-layer type photosensitive material according to claim 3, wherein the electric charge transferring layer contains 25 to 200 parts by weight of said phenylenediamine derivative (1) for 100 parts by weight of a binding resin.

5. The photosensitive material according to claim 4, wherein the electric charge generating layer contains, for 100 parts by weight of a binding resin, 5 to 500 parts by weight of one or more kinds of an electric charge generating material selected from the group consisting of selenium, selenium-tellurium, selenium-arsenic, amorphous silicon, pyrylium salt, azo compounds, disazo compounds, phthalocyanine compounds, anthanthrone compounds, indigo compounds, triphenylmethane compounds, threne compounds, toluidine compounds, pyrazoline compounds, perylene compounds, quinacridon compounds, and pyrrolopyrrole compounds.

6. The photosensitive material according to claim 5, wherein the electric charge generating material is an azo compound.

7. The photosensitive material according to claim 2, wherein the photosensitive layer is a single-layer type photosensitive layer comprised of an electric charge transferring material, an electric charge generating material and a binding resin.

8. The photosensitive material according to claim 7, wherein the single-layer type photosensitive layer contains 40 to 200 parts by weight of said phenylenediamine derivative (1) for 100 parts by weight of a binding resin.

9. The photosensitive material according to claim 8, wherein the single-layer type photosensitive layer contains, for 100 parts by weight of a binding resin, 2 to 20 parts by weight of one or more kinds of an electric charge generating material selected from the group consisting of selenium, selenium-tellurium, selenium-arsenic, amorphous silicon, pyrylium salt, azo compounds, disazo compounds, phthalocyanine compounds, anthanthrone compounds, indigo compounds, triphenylmethane compounds, threne compounds, toluidine compounds, pyrazoline compounds, perylene compounds, quinacridon compounds, and pyrrolopyrrole compounds.

10. The photosensitive material according to claim 9, wherein the electric charge generating material is an azo compound.

* * * * *